United States Patent [19]

Gozlan

[11] Patent Number: 5,721,380

[45] Date of Patent: Feb. 24, 1998

[54] DEVICE FOR FASTENING AN INSTRUMENT TO THE DRIVE HEAD OF A THREADED MEMBER, AND ITS APPLICATION TO A DYNAMOMETRIC APPLIANCE

[75] Inventor: Jean-Claude Gozlan, Boulogne, France

[73] Assignee: FACOM, Morangis Cedex, France

[21] Appl. No.: 444,041

[22] Filed: May 18, 1995

[30] Foreign Application Priority Data

May 18, 1994 [FR] France .................. 94 06 086

[51] Int. Cl.$^6$ ...................................... F16B 31/02
[52] U.S. Cl. ................................................. 73/761
[58] Field of Search ...................................... 73/761

[56] References Cited

U.S. PATENT DOCUMENTS

| 4,062,227 | 12/1977 | Heyman .............................. 73/761 |
| 4,294,122 | 10/1981 | Couchman . |
| 4,295,377 | 10/1981 | Couchman . |
| 4,846,001 | 7/1989 | Kibblewhite ....................... 73/761 |
| 5,392,654 | 2/1995 | Boyle ................................. 73/761 |

FOREIGN PATENT DOCUMENTS

| 0 381 791 | 8/1990 | European Pat. Off. . |
| 0073781 | 6/1977 | Japan . |
| 1054708 | 11/1983 | U.S.S.R. . |
| 2 037 430 | 7/1980 | United Kingdom . |
| 40 38 507 | 6/1992 | United Kingdom . |

Primary Examiner—Elizabeth L. Dougherty
Assistant Examiner—Max H. Noori
Attorney, Agent, or Firm—Wenderoth, Lind & Ponack

[57] ABSTRACT

A fastening device comprises a central core which, in use, is fixed together with an instrument and from which there extend claws equipped with a fastening mechanism for fastening the core onto the peripheral surface of a head. The claws, at least in one direction, leave free access to diametrically opposed portions of the head to enable driving of the head. The fastening mechanism is designed to interact with any region whatsoever of the peripheral side surfaces of the head.

22 Claims, 2 Drawing Sheets

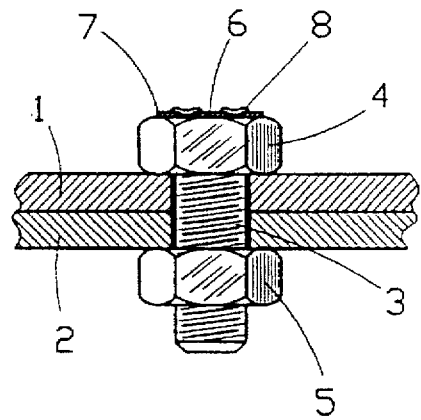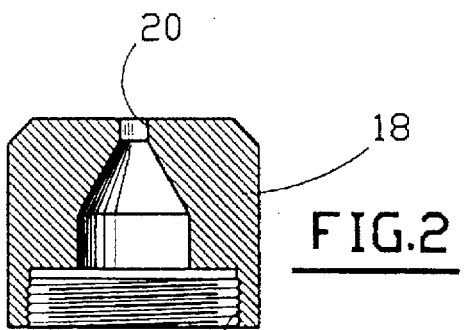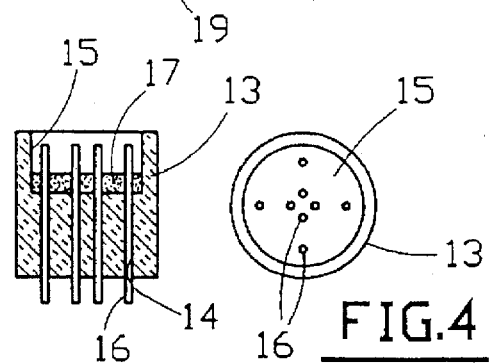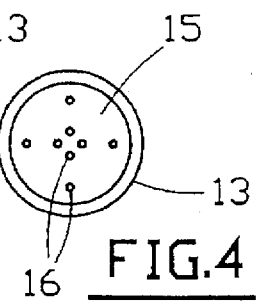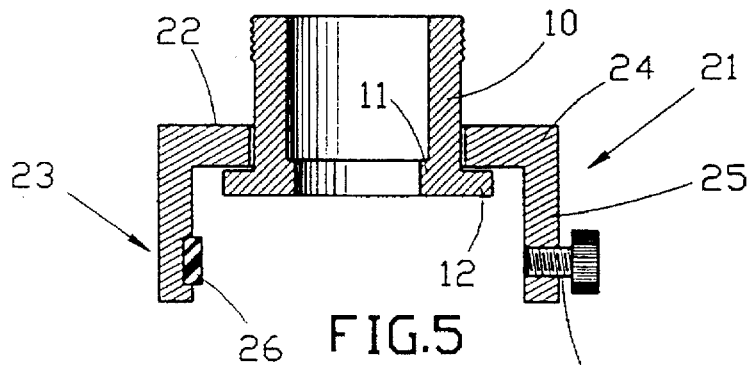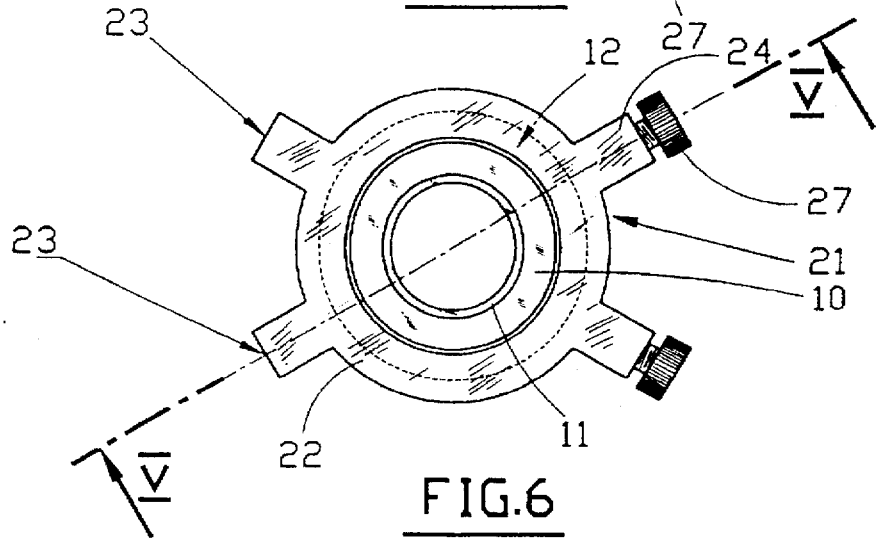

5,721,380

DEVICE FOR FASTENING AN INSTRUMENT TO THE DRIVE HEAD OF A THREADED MEMBER, AND ITS APPLICATION TO A DYNAMOMETRIC APPLIANCE

BACKGROUND OF THE INVENTION

The present invention relates to a device for fastening an instrument onto the outside of a drive head of a threaded member. It applies in particular to the fastening onto such a head of an instrument which forms part of a dynamometric measuring appliance.

Various methods have been proposed for the predetermined tightening of threaded members. Some of these methods comprise the use of transducers secured to the end surface of the drive head, and the fixing to this head of an instrument for measuring the indication from these transducers. In other methods, the transducers are borne by the instrument which is fixed onto the drive head. This may, for example, involve measurement using ultrasound, making it possible to measure the extension of the threaded member under tightening torque, or alternatively, measurement of the deformation of the head by means of contacts and piezoresistive elements bonded onto the head, as described in FR-A-2,696,215.

In such cases, an instrument forming part of the dynamometric measuring appliance connected to computing and display electronics has to be fixed to the head of the threaded member.

SUMMARY OF THE INVENTION

The object of the invention is to allow a particularly convenient use of these last-mentioned methods, not requiring the instrument to be removed in order to alter the degree of tightening of the threaded member.

To this end, the subject of the invention is a device for fastening an instrument onto the outside of the drive head of a threaded member, characterized in that it comprises a central core which, in use, is secured to the instrument and from which there extend claws equipped with means for fastening the core onto the peripheral surface of the head. These claws, at least in one direction, leave free access to diametrically opposed sides of the head to allow for driving of the head. The fastening means is designed to interact with any region whatsoever of the peripheral side surfaces of the head.

The fastening device according to the invention may include one or more of the following features:

- the fastening means comprise at least one element for bearing on one side or one corner of the head, provided on a first claw and a radial clamping screw screwed through a second claw diametrically opposite the first claw;
- when the device is intended for fastening the instrument onto a hexagon head, the fastening means comprise at least two bearing elements designed to interact respectively with two adjacent faces of the head, and two radial clamping screws which are respectively diametrically opposite these two bearing elements;
- when the device is intended for fastening the instrument onto a hexagon head, the fastening means comprise two bearing elements in the shape of a V with a 120° opening, borne by two diametrically opposed claws;
- one of the two bearing elements is secured to the claw which bears it, while the other is mounted so that it can rotate at the end of a radial clamping screw which is screwed through the other claw;

- the two claws are articulated to the core and extend beyond it, their ends opposite the bearing elements being joined together by a spacing-apart mechanism, particularly one with a hinge joint;
- the core includes a bearing part intended to clamp a radially projecting region of the instrument against the top surface of the head;
- the core surrounds a part of the instrument adjacent to the radially projecting region with radial clearance.

Another subject of the invention is a dynamometric appliance for determining the degree of tightness of a threaded member, the appliance comprising an instrument, and a device for fastening this instrument as defined hereinabove.

In one embodiment of this appliance, the core of the fastening device is interposed between an external collar of the instrument and a retaining member of the instrument.

BRIEF DESCRIPTION OF THE DRAWINGS

Embodiments of the invention will now be described with regard to the appended drawings, in which:

FIG. 1 represents the assembly of two components using a threaded member;

FIG. 2 is a view in longitudinal section of a component of a dynamometric measuring instrument for this assembly;

FIG. 3 is a view in longitudinal section of another component of this instrument;

FIG. 4 is a plan view of the component of FIG. 3;

FIG. 5 is a view in longitudinal section, sectioned on the line V—V of FIG. 6, of a third component of the same instrument and of the fastening device of the invention;

FIG. 6 is a plan view of the subject of FIG. 5;

DETAILED DESCRIPTION OF THE INVENTION

Figure 7:
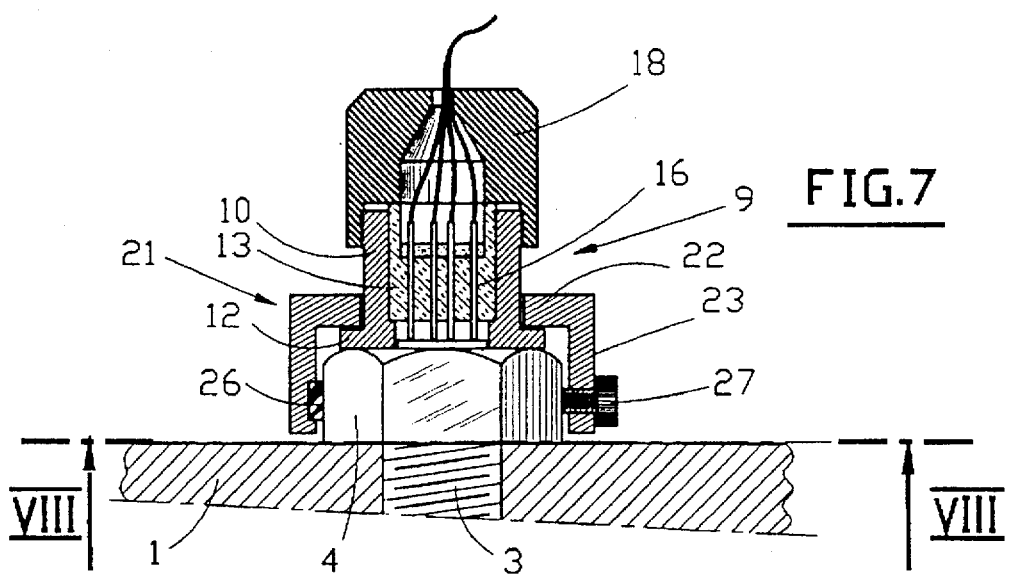
FIG. 7 represents a longitudinal section of the instrument fastened onto the assembly of FIG. 1, sectioned on the line VII—VII of FIG. 8.
Figure 8:
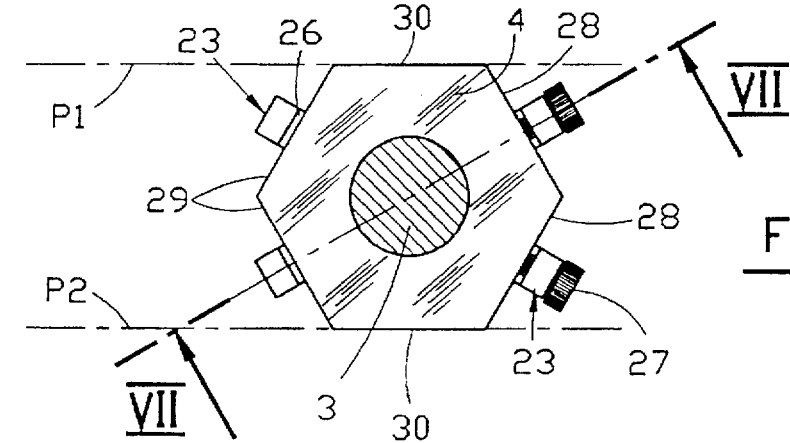
FIG. 8 is a section on the line VIII—VIII of FIG. 7.

FIG. 1 represents the assembly of two flat components 1 and 2 with parallel faces, using a bolt consisting of a screw 3 with a hexagon head 4 and of a lower nut 5. The degree of tightening of the bolt is determined by the method described in the abovementioned FR-A-2,696,215, from the measurement of the deformation of the head 4.

In order to measure this deformation, the upper face of the head 4 bears a central metal layer 6 and an annular metal layer 7, connected together by a piezo-resistive layer (contacts) 8. When the bolt is tightened, the deformation of the head 4 develops an electrical voltage between the layers 6 and 7, so that measurement of this voltage makes it possible, through appropriate computation, to determine the actual degree of tightening obtained.

The measuring appliance comprises, apart from computing and display electronics which have not been represented, a contact-bearing instrument 9 essentially consisting of three components:

- an externally threaded cylindrical support sleeve 10 (FIG. 5) which, at its base, has an internal collar 11 and an external collar 12;

a cylindrical contact block 13 made of an insulating material (FIGS. 3 and 4), pierced with eight vertical channels 14 and exhibiting a circular recess 15 in its upper face. A contact needle 16 is forcibly fit into each channel 14. Each needle extends upwards into the recess 15, where it is fixed by means of a layer of adhesive 17, and it also extends downwards. As can be seen in FIG. 4, four needles 16 are provided in the central region of the block 13, and four more needles are provided in the peripheral region of the recess 15; and a cap 18 (FIG. 2) which has a lower tapped bore 19 on the inside, and above this bore, a cavity which emerges at the top via a central orifice 20.

The instrument 9 is completed by a fastening device 21 which can be seen in FIGS. 5 to 8. This device comprises an annular core 22 which can be slipped with a small amount of clearance over the sleeve 10 and from which four L-shaped claws 23 extend. Each claw thus has a horizontal joining part 24 connected to the core and a main part 25 pointing downwards. Viewed in plan (FIGS. 6 and 8), the claws form two pairs of diametrically opposed claws. In each pair of the claws, one of the claws internally bears an elastomeric shoe 26 and the other of which has a tapped hole passing through it, into which a clamping screw 27 with a knurled head is screwed. The two claws of the same type are angularly spaced by approximately 45°, but the axes of the two screws 27, just like the normals to the lower faces of the shoes 26, form angles of 60° between them.

The instrument 9 is assembled by slipping the core 22 over the sleeve 10, then by introducing the block 13 into this sleeve, and then by fixing the block in place, bearing against the collar 11, by screwing the cap 18 onto the sleeve 10, such that the end shoulder of the bore 19 presses against the upper annular face of the block 13. Electric wires, indicated only in FIG. 7, are attached to and extend away from the upper end of each needle 16, pass through the orifice 20 and are connected to the electronics of the measuring appliance.

As can be seen in FIG. 7, when the instrument has been completely assembled, the core 22 is trapped, with a large amount of axial excursion, between the cap 18 and the external collar 12 of the sleeve 10.

In order to fasten the instrument 9 onto the head 4, the collar 12 is placed on the peripheral region of the upper face of this head, around the contacts 8, which brings the central contact needles 16 into contact with the central metal layer 6 and brings the external contact needles 16 into contact with the annular metal layer 7. With the screws 27 greatly unscrewed, the core 22 is brought against the collar 12, the four claws 23 therefore sliding freely along four faces of the head 4. By tightening the screws 27, they come into contact with two adjacent faces 28 (FIG. 8), and by reaction bring the shoes 26 against the two opposed faces 29. The position and size of the four claws and of the screws 27 are such that, viewed in plan, they fall wholly within the two planes P1, P2 defined by the two remaining parallel faces 30 of the head 4.

A gripper can therefore be placed in engagement with the two faces 30, which are freely accessible either from above or from the side, and the tightness of the bolt can be adjusted, following the indications displayed by the measuring appliance.

Figure 9:
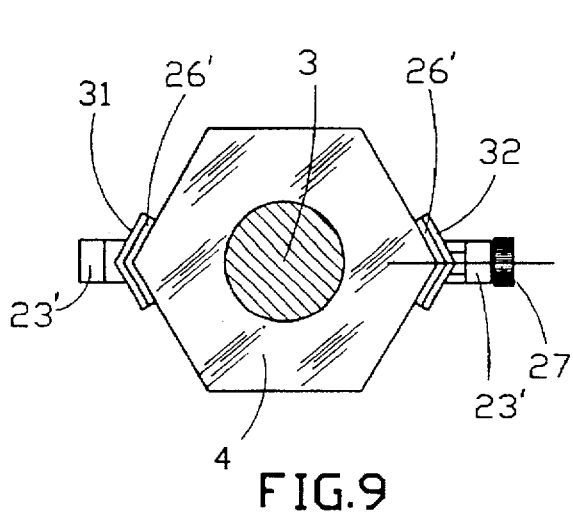
FIG. 9 is a view similar to FIG. 8 but of an alternative embodiment.

As an alternative (FIG. 9), the four claws 23 may be replaced by two diametrically opposed claws 23', one of which has a jaw 31 with a cross section in the shape of a V with a 120° opening, while the other claw has a radial clamping screw 27 passing through it, on the inside end of which screw another jaw 32 with a similar cross section is mounted so that it can rotate freely. Each jaw may, as before, be equipped with a flexible internal shoe 26' to increase the friction on the head 4.

Figure 10:
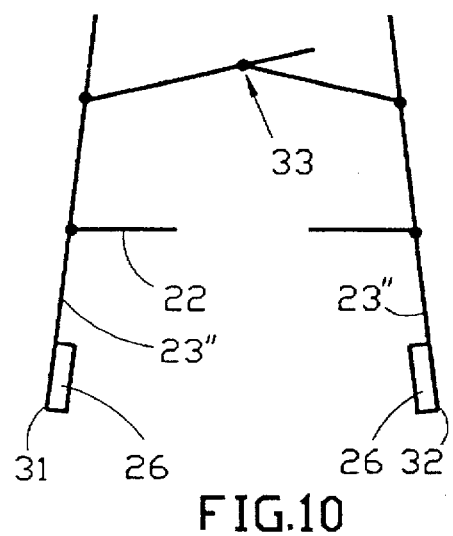
FIG. 10 diagrammatically represents another alternative of the fastening device, in vertical section.

As another alternative (FIG. 10), claws 23', two in number, may be articulated at diametrically opposed points of the core 22, extend upwards as far as the cap 18 and beyond, and have their top ends joined by a spacing-apart mechanism 33, for example as represented, to an articulated mechanism of the hinge joint type. In FIG. 10, shoes 26' have been represented at the lower end of the claws 23', which again have a V-shaped horizontal cross section with a 120° recess in order to interact with one corner of the hexagon head.

It will be understood that the invention also applies to the tightening of heads of screws or of nuts having male drive shapes other than a hexagon head. The shape of the claws is then matched to these drive shapes.

I claim:

1. A device for temporarily fixing an instrument to a drive head of a threaded member having a central axis, wherein the drive head has a peripheral sidewall parallel to the central axis of the threaded member, said device comprising:

a central core having a center axis;

a plurality of claws extending outwardly from said central core and including a fastening mechanism for removably fixing said central core to the peripheral sidewall of the drive head such that said center axis of said central core is parallel to the central axis of the threaded member, and so as to prevent axial movement of said central core relative to the drive head even without the provision of an axially directed external holding force; and wherein said claws are arranged on said central core in such a manner as to provide free access to diametrically opposed driving portions of the peripheral sidewall of the driving head.

2. A device as recited in claim 1, wherein said fastening mechanism is arranged so as to be located entirely between two mutually parallel planes which are parallel to said center axis of said central core and intersect, respectively, with radially outermost points of the diametrically opposed driving portions of the peripheral sidewall of the driving head, when said central core is fixed to the peripheral sidewall of the driving head.

3. A device as recited in claim 1, wherein said plurality of claws comprises a first claw and a second claw diametrically opposite said first claw and having a threaded through-hole; and said fastening mechanism comprises a bearing element provided on said first claw for bearing against the peripheral sidewall of the driving head, and a radial clamping screw threaded through said threaded through-hole of said second claw.

4. A device as recited in claim 1, wherein said fastening mechanism is configured for removably fixing said central core to a hexagonal drive head such that the peripheral sidewall includes six drive surfaces; and said fastening mechanism comprises two bearing elements arranged to bear against two adjacent ones of the six drive surfaces, respectively, and two radial clamping screws arranged diametrically opposite said two bearing elements, respectively.

5. A device as recited in claim 1, wherein said plurality of claws comprises two diametrically opposed claws; and said fastening mechanism comprises two V-shaped bearing elements borne by said claws, respectively, each of said V-shaped bearing elements having a 120° opening.

6. A device as recited in claim 5, wherein
one of said two claws has a threaded through-hole;
said fastening mechanism further includes a screw threaded through said threaded through-hole;
one of said two bearing elements is secured to said screw; and
the other of said two bearing elements is secured to the other of said two claws.

7. A device as recited in claim 1, wherein
said two claws are articulated to said central core, extend beyond said central core in opposing axial directions, have said two bearing elements located at first ends thereof, respectively, and are joined together at second ends thereof, respectively, to define a spacing-apart mechanism between said two claws.

8. A device as recited in claim 7, wherein
said spacing-apart mechanism comprises a toggle mechanism.

9. A device as recited in claim 1, wherein
said central core includes a bearing part intended to clamp, in use, a radially projecting region of the instrument against a top surface of the drive head.

10. A device as recited in claim 9, wherein
said central core is configured to surround a part of the instrument adjacent the radially projecting region thereof, with radial clearance between said central core and the instrument.

11. A dynamometric appliance for determining a degree of tightening of a threaded member having a central axis and a drive head including a peripheral sidewall parallel to the central axis of the threaded member, said dynamometric appliance comprising
an instrument, and a device for temporarily fixing said instrument to the drive head of the threaded member, said device comprising:
a central core having a center axis;
a plurality of claws extending outwardly from said central core and including a fastening mechanism for removably fixing said central core to the peripheral sidewall of the drive head such that said center axis of said central core is parallel to the central axis of the threaded member, and so as to prevent axial movement of said central core relative to the drive head even without the provision of an axially directed external holding force; and
wherein said claws are arranged on said central core in such a manner as to provide free access to diametrically opposed driving portions of the peripheral sidewall of the driving head.

12. A dynamometric appliance as recited in claim 11, wherein
said instrument comprises a sleeve having an external collar, and a retaining member mounted to said sleeve; and
said central core of said device is interposed between said external collar and said retaining member.

13. A dynamometric appliance as recited in claim 11 wherein
said instrument comprises at least one contact needle.

14. A dynamometric appliance as recited in claim 11, wherein
said fastening mechanism is arranged so as to be located entirely between two mutually parallel planes which are parallel to said center axis of said central core and intersect, respectively, with radially outermost points of the diametrically opposed driving portions of the peripheral sidewall of the driving head, when said central core is fixed to the peripheral sidewall of the driving head.

15. A dynamometric appliance as recited in claim 11, wherein
said plurality of claws comprises a first claw and a second claw diametrically opposite said first claw and having a threaded through-hole; and
said fastening mechanism comprises a bearing element provided on said first claw for bearing against the peripheral sidewall of the driving head, and a radial clamping screw threaded through said threaded through-hole of said second claw.

16. A dynamometric appliance as recited in claim 11, wherein
said fastening mechanism is configured for removably fixing said central core to a hexagonal drive head such that the peripheral sidewall includes six drive surfaces; and
said fastening mechanism comprises two bearing elements arranged to bear against two adjacent ones of the six drive surfaces, respectively, and two radial clamping screws arranged diametrically opposite said two bearing elements, respectively.

17. A dynamometric appliance as recited in claim 11, wherein
said plurality of claws comprises two diametrically opposed claws; and
said fastening mechanism comprises two V-shaped bearing elements borne by said claws, respectively, each of said V-shaped bearing elements having a 120° opening.

18. A dynamometric appliance as recited in claim 17, wherein
one of said two claws has a threaded through-hole;
said fastening mechanism further includes a screw threaded through said threaded through-hole;
one of said two bearing elements is secured to said screw; and
the other of said two bearing elements is secured to the other of said two claws.

19. A dynamometric appliance as recited in claim 11, wherein
said two claws are articulated to said central core, extend beyond said central core in opposing axial directions, have said two bearing elements located at first ends thereof, respectively, and are joined together at second ends thereof, respectively, to define a spacing-apart mechanism between said two claws.

20. A dynamometric appliance as recited in claim 19, wherein
said spacing-apart mechanism comprises a toggle mechanism.

21. A dynamometric appliance as recited in claim 11, wherein
said central core includes a bearing part intended to clamp, in use, a radially projecting region of the instrument against a top surface of the drive head.

22. A dynamometric appliance as recited in claim 21, wherein
said central core is configured to surround a part of the instrument adjacent the radially projecting region thereof, with radial clearance between said central core and the instrument.

* * * * *